(12) United States Patent
Huang

(10) Patent No.: US 8,329,161 B2
(45) Date of Patent: Dec. 11, 2012

(54) RED BLOOD CELL-DERIVED VESICLES AS A NANOPARTICLE DRUG DELIVERY SYSTEM

(75) Inventor: Dong-Ming Huang, Taoyuan (TW)

(73) Assignee: National Health Research Institutes, Miaoli County (TW)

( * ) Notice: Subject to any disclaimer, the term of this patent is extended or adjusted under 35 U.S.C. 154(b) by 741 days.

(21) Appl. No.: 12/405,206

(22) Filed: Mar. 16, 2009

(65) Prior Publication Data

US 2009/0274630 A1 Nov. 5, 2009

Related U.S. Application Data

(60) Provisional application No. 61/049,473, filed on May 1, 2008.

(51) Int. Cl.
*A01N 63/00* (2006.01)
*A61B 5/055* (2006.01)
(52) U.S. Cl. .................. 424/93.1; 424/9.3; 977/905
(58) Field of Classification Search ............... 424/93.1, 424/3; 977/905
See application file for complete search history.

(56) References Cited

U.S. PATENT DOCUMENTS 6,645,464 B1 * 11/2003 Hainfeld ..................... 424/1.29
2002/0034537 A1 * 3/2002 Schulze et al. .............. 424/450
2008/0089836 A1 * 4/2008 Hainfeld ..................... 424/1.11

OTHER PUBLICATIONS van den Bos et al. Cell Transplantation. 12(7):743-756, 2003.*
Magnani, M., L. Rossi, et al. (1992) "Targeting antiretroviral nucleoside analogues in phosphorylated form to macrophages: in vitro and in vivo studies." Proc Natl Acad Sci U S A 89(14): 6477-81.
Leonards, K. S. and S. Ohki (1983) "Isolation and characterization of large (0.5-1.0 micron) cytoskeleton-free vesicles from human and rabbit erythrocytes." Biochim Biophys Acta 728(3): 383-93.
Millan, C. G. et al. (2004) "Drug, enzyme and peptide delivery using erythrocytes as carriers." Journal of Controlled Release 95: 27-49.
Hamidi, M. and Tajerzadeh, H. (2003) "Carrier erythrocytes: An overview." Drug Delivery 10: 9-20.
Magnani et al. (1996) "Synthesis and targeted delivery of an azidothymidine homodinucleotide conferring protection to macrophages against retroviral infection" Proc. Natl. Acad. Sci. USA vol. 93, pp. 4403-4408.

* cited by examiner

*Primary Examiner* — Marcia S Noble
(74) *Attorney, Agent, or Firm* — Hsiu-Ming Saunders; Intellectual Property Connections, Inc.

(57) ABSTRACT

Red blood cell-derived vesicles (RDV) as a nanoparticle drug delivery system. The RDV are smaller than one micrometer, capable of encapsulating and delivering an exogenous substance into cells. The substance may be at least one selected from the group consisting of fluorophores, nucleic acids, superparamagnetic compounds and therapeutic agents. The RDV are capable of delivering encapsulated substances into cells including stem cells. The delivered substance within the cell or stem cell may be traced or tracked using a suitable device either in vitro or in vivo.

18 Claims, 12 Drawing Sheets

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
taatacgact cactataggg                    20

<210> SEQ ID NO 2
<211> LENGTH: 30
<212> TYPE: DNA
<213> ORGANISM: Artificial Sequence
<220> FEATURE:
<223> OTHER INFORMATION: Reverse primer

<400> SEQUENCE: 2
gactcgagct agtcgtgctt gagagtgagg          30

<210> SEQ ID NO 3
<211> LENGTH: 572
<212> TYPE: DNA
<213> ORGANISM: Artificial Sequence

```
<220> FEATURE:
<223> OTHER INFORMATION: 5'-T7-ferritin-3'-Xho ds DNA

<400> SEQUENCE: 3
taatacgact cactataggg atgacctctc agattcgtca gaattattcc accgaggtgg      60
aagctgccgt gaaccgcctg gtcaacttgc acctgcgggc ctcctacacc tacctctctc     120
tgggcttctt ttttgatcgg gatgacgtgg ctctggaggg cgtaggccac ttcttccgcg     180
aattggccga ggagaagcgc gagggcgcgg agcgtctcct cgagtttcag aacgatcgcg     240
ggggccgtgc actcttccag gatgtgcaga agccatctca agatgaatgg ggtaaaaccc     300
aggaggccat ggaagctgcc ttggccatgg agaagaacct gaatcaggcc ctcttggatc     360
tgcatgccct gggttctgcc cgcgcggacc ctcatctctg tgacttcctg gaaagccact     420
atctggataa ggaggtgaaa ctcatcaaga agatgggcaa ccatctgacc aacctccgca     480
gggtggcggg gccacaacca gcgcagactg gcgcgcccca ggggtctctg ggcgagtatc     540
tctttgagcg cctcactctc aagcacgact ag                                   572

<210> SEQ ID NO 4
<211> LENGTH: 20
<212> TYPE: DNA
<213> ORGANISM: Artificial Sequence
<220> FEATURE:
<223> OTHER INFORMATION: T7 promoter region ss DNA

<400> SEQUENCE: 4
taatacgact cactataggg                                                  20

<210> SEQ ID NO 5
<211> LENGTH: 21
<212> TYPE: DNA
<213> ORGANISM: Artificial Sequence
<220> FEATURE:
<223> OTHER INFORMATION: combined DNA/RNA for siRNA sense

<400> SEQUENCE: 5
uucuccgaac gugucacgut t                                                21

<210> SEQ ID NO 6
<211> LENGTH: 21
<212> TYPE: DNA
<213> ORGANISM: Artificial Sequence
<220> FEATURE:
<223> OTHER INFORMATION: combined DNA/RNA for siRNA antisense

<400> SEQUENCE: 6
acgugacacg uucggagaat t                                                21
```

RED BLOOD CELL-DERIVED VESICLES AS A NANOPARTICLE DRUG DELIVERY SYSTEM

REFERENCE TO RELATED APPLICATION

The application claims the priority of U.S. provisional application No. 61/049,473, filed May 1, 2008, which is incorporated herein in its entirety by reference.

FIELD OF THE INVENTION

The present invention relates generally to nanoparticles, and more specifically to a nanoparticle drug delivery system.

BACKGROUND OF THE INVENTION

Nanoparticles for the purpose of drug delivery are defined as smaller than one micron (<1 μm) colloidal particles. This definition includes monolithic nanoparticles (nanospheres) in which the drug is adsorbed, dissolved, or dispersed throughout the matrix, and nanocapsules in which the drug is confined to an aqueous or oily core surrounded by a shell-like wall. Alternatively, the drug can be covalently attached to the surface or into the matrix. Nanoparticles are made from biocompatible and biodegradable materials such as polymers, either natural (e.g., gelatin, albumin) or synthetic (e.g., polylactides, polyalkylcyanoacrylates), or solid lipids. In the body, the drug loaded in nanoparticles is usually released from the matrix by diffusion, swelling, erosion, or degradation (Gelperina et al. (2005) "The Potential Advantages of Nanoparticle Drug Delivery Systems in Chemotherapy of Tuberculosis" *American Journal of Respiratory and Critical Care Medicine* Vol 172, 1487-1490).

While the unique characteristics (i.e., small size and greater surface-area-to-mass ratio and physicochemical properties) of nanoparticles offer exciting promises in biomedical applications, they also have prompted worries about their potential toxicities. For example in stem cell tracking, superparamagnetic iron oxide (SPIO) nanoparticles have been recognized as a promising tool to intracellular labeling of cells for cellular magnetic resonance imaging (MRI), which plays a key role for developing successful stem cell therapies. Because of the low cellular internalizing efficiency of native SPIO nanoparticles, several modifications of SPIO nanoparticles have been reported to improve the cellular internalization of SPIO nanoparticles. Potential hazards associated with these modifications to stem cells are highly considered. The fact that nanoparticles are manufactured and xenogeneic is a perpetual issue of potential hazard in nanomedical applications.

Erythrocytes have been exploited extensively for their potential applications as carriers of different bioactive substances because of biocompatibility and biodegradability. These carrier erythrocytes may be employed to serve as a reservoir for sustained release or to direct drugs to the reticuloendothelial system (RES), or both.

Red blood cells are about 7.5-8 μm in diameter, which are larger than nanoparticles. Few cells other than macrophages are capable of internalizing particles this large. Generating submicrometer RDV that contain and encapsulate substances can eliminate these problems and fulfill needs for a well-defined nanoparticle drug delivery system.

SUMMARY OF THE INVENTION

In one aspect, the invention relates to an isolated red blood cell-derived vesicle (RDV) that contains an encapsulated exogenous substance.

In one embodiment of the invention, the isolated RDV has a diameter of no more than 500, 400, 350, or 300 nanometers. The encapsulated exogenous substance may include at least one substance selected from the group consisting of a fluorophore, a nucleic acid, a superparamagnetic compound and a therapeutic agent. The isolated RDV is capable of entering cells other than macrophages, and without any modification on the surface membrane thereof.

In another aspect, the invention relates to a method of delivering a substance into a cell, which includes the following steps: (a) contacting the cell with an isolated RDV that contains an encapsulated exogenous substance; and (b) allowing the cell to internalize the RDV to obtain an RDV-internalized cell, thereby delivering the substance into the cell.

In one embodiment of the method invention, it includes the step of contacting the cell with an isolated RDV having a diameter of no more than 500, 400, 350, or 300 nanometers.

In another embodiment of the invention, the method includes the step of contacting the cell with an isolated RDV that contains an encapsulated exogenous substance which is at least one selected from the group consisting of fluorophores, nucleic acids, peptides, polysaccharides, superparamagnetic compounds and therapeutic agents. The cell is at least one selected from the group consisting of primary cells, cancer cells and stem cells. In one embodiment of the method invention, the cell and the RDV included therein are autologous.

In one embodiment of the invention, the method includes the step of contacting a stem cell with an isolated RDV that encapsulates a superparamagnetic compound. The method invention may further include the step of tracking the superparamagnetic compound within the stem cell by MRI.

In another embodiment of the invention, the method includes the step of administering to a patient the RDV-internalized stem cell, in which the stem cell and RDV are autologous to the patient. The method may further include the step of in vivo tracking the superparamagnetic compound within the stem cell by MRI. The superparamagnetic compounds include $Fe_3O_4$.

Further in another aspect, the invention relates to a method for preparing isolated red blood cell-derived vesicles (RDV), which include the following steps: (a) preparing red blood cells (RBC) from a blood sample; (b) preparing 1 M $CaCl_2$, 390 mM EDTA and double deionized water ($ddH_2O$); and (c) admixing the RBC, $CaCl_2$, EDTA and $ddH_2O$ according to the following volume ratio to obtain a mixture containing RDV: (i) $CaCl_2$:EDTA=1:1; (ii) RBC volume is more than 2.5 times, but less than 5 times, of that of $CaCl_2$; and (iii) $ddH_2O$'s volume is the difference between RBC and the sum of $CaCl_2$:EDTA.

In one embodiment of the invention, the above step (c) is performed at a temperature below 50° C. In another embodiment of the invention, the aforementioned method further includes the step of centrifugating the RDV-containing mixture to collect the isolated RDV.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention.

Wherever possible, the same reference numbers are used throughout the drawings to refer to the same or like elements of an embodiment.

DETAILED DESCRIPTION OF THE INVENTION

Definitions

Figure 1A:
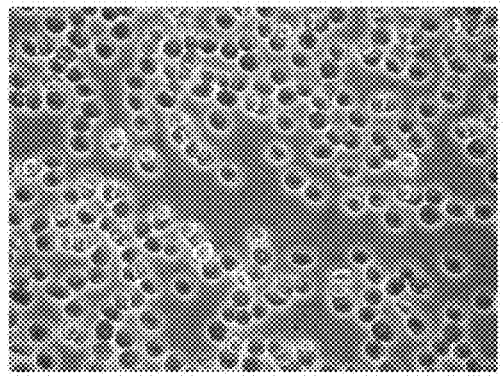
FIGS. 1A-1E are microscopic images of erythrocytes in various solutions. A: RBC in phosphate buffered saline (PBS); B: RBC in an equal volume of water; C: RBC in a lower concentration of $Ca^{2+}$-EDTA, beginning to form buds (as indicated by arrows); D: RBC in a moderate concentration of $Ca^{2+}$-EDTA, forming abundant RDV; E: extensive erythrocyte lysis in a high concentration of $Ca^{2+}$-EDTA. Scale bar: 50 μm.
Figure 1B:
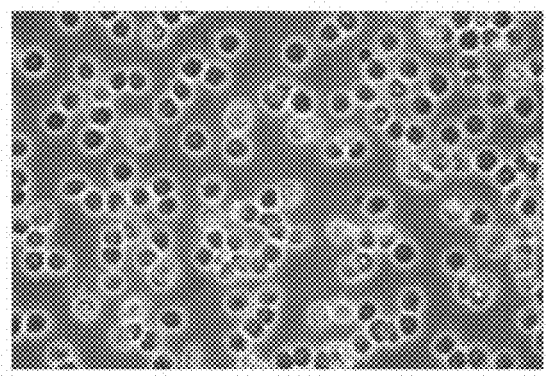

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "xenogeneic" refers to derived or obtained from an organism of a different species.

As used herein, "exogenous" refers to originating from outside; derived externally.

As used herein, "autologous" refers to from the same organism.

As used herein, "primary cells" refers to the cells taken directly from the living organism (e.g. biopsy material).

The invention relates to RDV and their applications as a drug delivery system. RDV exhibit properties including capacity for uptake by cells and carrier ability of acting as a nanocarrier for SPIO for intracellular labeling and MRI of stem cells. Moreover, the excellent biocompatibility of autologous RDV would resolve the nanotoxicology issue related to applications of nanoparticles in biomedicine.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the

Methods

1. Preparation of RDV

RDV were prepared using $Ca^{2+}$-EDTA (Leonards, K. S. and S. Ohki (1983) "Isolation and characterization of large (0.5-1.0 micron) cytoskeleton-free vesicles from human and rabbit erythrocytes." *Biochim Biophys Acta* 728(3): 383-93). Briefly, 30 ml of venous blood samples from 5 male and 5 female healthy donors were collected and mixed with heparin (50 U/ml). The blood samples were centrifuged at 1,700 g at 4° C. for 10 min. Plasma was removed. Two hundred microliters of erythrocytes (about 2-2.4×10⁶ RBC) were mixed with various amounts of 1 M $CaCl_2$ and 390 mM EDTA (Table 1) at 45° C. for 30 min to produce RDV. All the treated erythrocytes were observed under phase contrast microscope (Olympus). The mixture was in turn centrifuged at 1,700 g for 10 min at 4° C. Supernatant was collected and centrifuged again at 16,000 g for 10 min at 4° C. to obtain ultra small vesicles (around 200 nm). After the centrifugation, the pellet was washed twice with PBS and resuspended in PBS.

TABLE 1*

| | Tube No. | | | | | | | | | | |
|---|---|---|---|---|---|---|---|---|---|---|---|
| | 1 | 2 | 3 | 4 | 5 | 6 | 7 | 8 | 9 | 10 | 11 |
| Erythrocytes | 200 | 200 | 200 | 200 | 200 | 200 | 200 | 200 | 200 | 200 | 200 |
| $CaCl_2$ (1M) | 0 | 10 | 20 | 30 | 40 | 50 | 60 | 70 | 80 | 90 | 100 |
| EDTA (309 mM) | 0 | 10 | 20 | 30 | 40 | 50 | 60 | 70 | 80 | 90 | 100 |
| dd $H_2O$ | 200 | 180 | 160 | 140 | 120 | 100 | 80 | 60 | 40 | 20 | 100 |

*The unit is in microliter (µl).
dd $H_2O$ refers to double deionized water.

2. Analysis of Vesicle Size and Iron Content

The iron concentration of RDV was analyzed with Iron-SL kit (Diagnostic Chemicals Limited) in accordance with the manufacturer's instructions. The chromogen Ferene® in the Iron-SL kit reacted with ferrous iron to form a blue chromophore that absorbed light at 595 nm. Data were collected with an ELISA plate reader (Infinite M 200, TECAN) by measuring the absorbance (OD) at 595 nm.

The size of RDV was estimated with a particle size analyzer (90 plus, Brookhaeven, Instrument Corporation) in accordance with the manufacturer's protocol. The diameter of RDV was also measured using transmission electron microscopy (TEM). The RDV were directly loaded onto the grid (Electron Microscopy Sciences) and extra PBS was absorbed by nitrocellulose membrane. The loaded grid was soaked at room temperature overnight and then observed by TEM (Hitachi H-7650) according to the standard procedure.

3. Encapsulation of Substances Into RDV

In general, RDV (100 µg in 10 µl of PBS) and 10 µl of solutions containing substances to be encapsulated were incubated with 100 µl of hypoosmotic lysing buffer ($Na_2HPO_4$/$NaH_2PO_4$, 20 mM, pH 8) for 1 hr at 40° C. The mixtures were centrifuged at 16,000×g for 10 min at 4° C. to pellet the vesicles to separate them from the solutions containing the non-encapsulated substances. To wash the vesicles, the pellets were resuspended in PBS and centrifuged 16,000×g for 10 min at 4° C. After a second wash, the vesicles were resuspended in PBS a final time before use Substances that were encapsulated are illustrated below.

TABLE 2

| Compound | Type | Final concentration |
|---|---|---|
| $Fe_3O_4$ | magnetite | 100 µg/100 µl |
| Fluorescein isothocyanate (FITC) | Fluorescent dye | 20 nmole/100 µl |
| FITC-Taxol | Fluorescent labeled anticancer drug | 10 µg/100 µl |
| Oregon Green® 488 Taxol (FITC-taxol; Green® 488 Flutax-2; Invitrogen) | Fluorescent labeled anticancer drug | 10 µg/100 µl |
| FAM-dsDNA | Fluorescent labeled double-stranded DNA | 1 µg/100 µl |
| FAM-ssDNA T7 | Fluorescent labeled single-stranded DNA | 0.05 nmole/100 µl |
| FAM-siRNA | Fluorescent labeled si-RNA | 0.1 nmole/100 µl |

The dsDNA product (SEQ ID 3) was amplified by PCR with the forward primer, carboxy fluorescein (FAM)-T7 (FAM-5'-TAATACGACTCACTATAGGG; SEQ ID NO: 1; PURIGO BIOTECH, Taiwan) and the reverse primer ferritin-3' Xho (GACTCGAGCTAGTCGTGCTTGAGAGTGAGG; SEQ ID NO: 2; MDBio, Taiwan). The forward primer carboxy fluorescein (FAM)-T7 was a bacteriophage T7 promoter region DNA with the 5' end being labeled with FAM; and the reverse primer ferritin-3' Xho was a Xho I restriction enzyme sequence at 3' end of ferritin for subsequent cloning purpose. The PCR conditions were as follows: 1×PCR buffer (50 mM KCl, 10 mM Tris-HCl, pH 8.8, 2.5 mM $MgCl_2$, and 0.1%, Triton X-100), dNTPs (0.05 mM), forward and reverse primers (0.1 µM each), template DNA (1 ng/µl), and Taq DNA polymerase (0.02 U/µl); the PCR thermocycling profile: 1 min at 94° C., 1 min at 55° C. for 30 PCR cycles and 2 min at 72° C. The final PCR product was labeled with FAM (MD-Bio, Taiwan). For FAM-ssDNAT7 oligonucleotide, FAM-5'-TAATACGACTCACTATAGGG (SEQ ID NO: 4) was synthesized by PURIGO BIOTECH, Taiwan. For FAM-siRNA, the negative control FAM, i.e., sense FAM-5'-UUCUC-CGAACGUGUCACGUTT-3' (SEQ ID NO: 5), and the antisense: 5'-ACGUGACACGUUCGGAGAATT-3' (SEQ ID NO: 6) were synthesized by MDBio, Taiwan. Substance-encapsulated RDV were analyzed using MRI and flow cytometry.

Other Substances Encapsulated Into RDV

Other cargos that were tested and able to be encapsulated into RDV included iron oxide (T2 contrast), gadolinium (Gd, a T1 contrast agent for MRI), paclitaxel, doxorubicin hydrochloride, protoporphyrin IX (a photosensitizor for phototherapy), 5-aminolevulinic acid hydrochloride (a prodrug of 5-Aminolevulinic acid hydrochloride), 1-B-D-arabinofuranosylcytosine (Ara-c), and all-tirans-Retinoic acid (ATRA, Tretinoin, Vitamin A acid). Peptides including insulin, EPO, interleukin, EGF, hormone, cytokine, etc., and polysaccharides including streptozotocin, topiramate, lactulose, 4-Guaidino-Neu5Acen, etc., may also be encapsulated into RDV.

Each cargo had its own characteristics and the determinations of encapsulation efficiency were very different. Thus, it could hardly conclude which cargo had the best encapsulation efficiency.

It was found that each substance encapsulation efficiency mainly depended on its own characteristics. It appeared that more hydrophobic drugs were more easily to be encapsulated into RDV. Different protocols were used for different substance encapsulation. Factors that might help overcome the difficulties and increase encapsulation efficiency included addition of ATP and glucose in the hypotonic solution (Magnani, M., L. Rossi, et al. (1992) "Targeting antiretroviral nucleoside analogues in phosphorylated form to macrophages: in vitro and in vivo studies" *Proc Natl Acad Sci* USA 89 (14): 6477-81). It appeared that there had not a one-size-fits-all optimal protocol for encapsulating all cargos.

$Fe_3O_4$ $Fe_3O_4$ stock solution (100 μg/10 μl) was prepared by mixing 100 μg of $Fe_3O_4$ (Taiwan Advanced Nanotech Inc., Amino-TANBeads/USPIO-101) with 10 μl of dd $H_2O$. To test whether $Fe_3O_4$ alone would enter cells, 10 μl of the stock solution were mixed with 90 μl of hypotonic solution and 2 ml of DMEM for treatment with cells.

Encapsulation of Fe3O4 Into RDV $Fe_3O_4$-encapsulated RDV were prepared as follows: RDV (100 μg in 10 μl PBS) were mixed with 10 μl of $Fe_3O_4$ stock solution (100 μg/10 μl) and 80 μl hypotonic solution, and incubated for 1 h at 4° C. The resulted $Fe_3O_4$-encapsulated RDV mixture was added into 2 ml DMEM before treatment of cells.

Delivering $Fe_3O_4$ Into Cells

To test RDV competency in delivering $Fe_3O_4$ into cells, $1.2\times10^5$ hMSCs were treated with vehicle, RDV, $Fe_3O_4$, $Fe_3O_4$ plus RDV or $Fe_3O_4$-encapsulated RDV for 1 h at 37° C. Cells were washed twice with PBS and harvested by trypsinization and centrifugation for 5 min at 1,200 g. The cells were harvested as cell pellets in eppendorf tubes and then processed for MRI by 1.5-T MRI system. The cells treated with $Fe_3O_4$-encapsulated RDV could be MR imaged, which would prove that RDV could carry $Fe_3O_4$ and deliver $Fe_3O_4$ into stem cells.

4. Delivery of Substance-Encapsulated RDV Into Cells

NIH3T3 cell lines (a mouse embryonic fibroblast) and B16 cells (a mouse melanoma cell line) were grown in DMEM supplemented with 10% fetal bovine serum (FBS, Biological Industries) and 1× penicillin-streptomycin-amphotericine B (Biological Industries).

hMSCs were isolated from bone marrow of normal donors. Briefly, the bone marrow aspirate was added to low-glucose DMEM containing 25 U/ml heparin in 1:1 ratio (v/v), fractionated by Ficoll-Paque density gradient centrifugation. The hMSCs-enriched low-density fraction was collected, rinsed with DMEM, and plated in T25 flasks at $5\times10^7$ nucleated cells per flask in 5 ml of regular growth medium consisting of low-glucose DMEM supplemented with 10% fetal bovine serum (FBS; HyClone, Logan, Utah), 4 mM L-glutamine, 100 U/ml penicillin, and 100 μg/ml streptomycin (Sigma-Aldrich). During the first two-week incubation for cell adherence and initial expansion, 5 ml of fresh growth medium was added twice weekly for the first week. Medium changes were carried out twice weekly. When adherent cells reached about 60% to 70% confluence, they were detached with 0.25% trypsin-EDTA (ethylenediamineteraacetic acid; GIBCO) and replated at 1:3 in regular growth medium to allow for continued passage. All cultures were kept in atmosphere of 5% CO2, 95% air at 37° C.

To deliver RDV into cells, 100 μg of RDV in 10 μl of PBS were mixed with 90 μl of hypotonic solution (i.e., hypoosmotic lysing buffer as described above). The mixture (100 μl) was added into 2 ml of DMEM to form a suspension preparation of RDV. The RDV suspension was loaded onto NIH3T3 cells ($1.2\times10^5$ cells) grown on slides and incubated for various time periods.

B16 or hMSCs ($1.2\times10^5$ cells) were grown on poly-L-lysine-coated glass cover slides in 2 ml growth medium (DMEM) and treated with the RDV suspension for one hour. For control, cells were incubated with vehicle, which was made by adding 100 μl hypotonic solution into2 ml DMEM.

Tracking RDV Entry Into Cells by MRI

After being loaded with RDV, NH3T3 cells were washed in PBS and placed in PCR tubes, which were soaked in water and cell uptake of RDV were observed by MRI.

Tracking Exogenous $Fe_3O_4$ Entry Into Cells by MRI

After treatment with $Fe_3O_4$-encapsulated RDV, cells were pelleted to the bottom of eppendorf tubes by centrifugation. The tubes were placed in a water tank. The tank was then placed in an eight-channel head coil. MRI was performed using clinical 1.5-T MR imaging System (Signa excite, GE Healthcare, USA). For MR imaging, two-dimension T2-weighted Fast spin echo pulse sequences provided by the vendor (FSE-XL/90) were used (TR/TE¼667/11.9 ms). The slice thickness was 1.4 mm with 0.03 mm gap and the field of view (FOV) was 16T8 cm. Total scan time was 3 min and 47 s at the number of excitation (NEX) of 6. The images were then analyzed at the workstation provided by GE healthcare.

MR Imaging of Magnetically Labeled hMSCs in Vivo

Male balb/c mice (6 weeks of age) were obtained from the Animal Center of National Taiwan University (Taiwan) and maintained in accordance with the procedures and guidelines of the Institutional Animal Care and Use Committee. hMSCs treated with vehicle or $Fe_3O_4$-encapsulated RDV were harvested by trypsinization and suspended in PBS. Adult male nude mouse was anesthetized by injecting a mixture of ketamine (100 mg/kg) and xylazine (5 mg/kg) into intraperitoneal space. Stereotaxic injection of hMSCs was performed with a NARISHIGE apparatus and a WPI syringe with a bevel-tipped 26.5-gauge needle. The injection coordinates were (relative to bregma [AP], the midline [ML] and the dura [DV]): AP: −1 mm, ML: 1 mm, DV: 2 mm. Injections were performed at the rate of 1 μL/min and the needle was left in place for 5 min before withdrawal. hMSCs treated with vehicle and hMSCs treated with $Fe_3O_4$-encapsulated RDV were injected into the right and left side brain of the mice, respectively. After hMSCs implantation, MRI was performed using clinical 1.5-T MR System (Signa Excite, GE Healthcare, USA). Under gas anesthesia with 2% isoflurane, the mouse was placed to a home-made resonance coil with an inner diameter of 3.7 cm. Fast spin echo pulse (FSE-XL) sequences provided by the vendor were used (TR/TE=4000/101.4 ms, Matrix size=288×192). The slice thickness was 0.8 mm with 0.2 mm gap and the field of view (FOV) was 5×2.5 cm. Total scan time was 3 min and 20 sec at the NEX of 8. The images were analysed at the workstation provided by GE healthcare.

Tracking Encapsulated Flouorophore by Flow Cytomery

FITC-encapsulated RDV were analyzed by flow cytometry (BD FACSCalibur) based on standard procedure to evaluate the extent of substance encapsulation efficiency. Cells that had been loaded with FITC-encapsulated RDV were also analyzed by flow cytometry to evaluate RDV drug delivery competency.

Tracking Encapsulated Fluorophore by Confocal Microscopy The cells were incubated with 20 µl of Lysotracker (Invitrogen) (1% in medium) and then fixed in 4% Paraformaldehyde/400 mM sucrose/PBS. Cellular entrance of fluorophore-encapsulated RDV into cells was observed and acquired by confocal microscopy (Leica).

5. Differentiations of RDV-Treated Stem Cells hMSCs were loaded with RDV and grown in normal, adipogenic and osteogenic medium, respectively. Normal medium consists of low-glucose Dulbecco's modified Eagle's medium (DMEM; Gibco) supplemented with 10% FBS (HyClone, Logan, Utah), 4 mM L-glutamine, 100 U/ml penicillin, and 100 µg/ml streptomycin (Sigma-Aldrich). Adipogenic medium consists of high-glucose DMEM supplemented with isobutyl-1-methylxanthine (0.5 mM, IBMX; Sigma-Aldrich), dexamethasone (1 mM, Sigma-Aldrich), insulin (10 ngmLS1, Sigma-Aldrich), indomethacin (50 mM, Sigma-Aldrich), and FBS (10%). Osteogenic medium consists of α-MEM (GIBCO) supplemented with dexamethasone (1 mM), β-glycerolpilosphate (50 mM, Sigma-Aldrich), and ascorbic acid (50 mgmLS1, AsA; Sigma-Aldrich).

Results

Figure 1C:
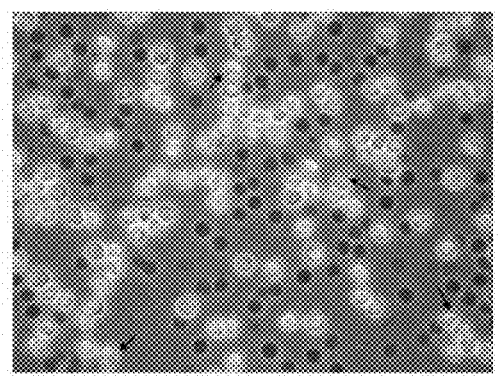
Figure 1D:
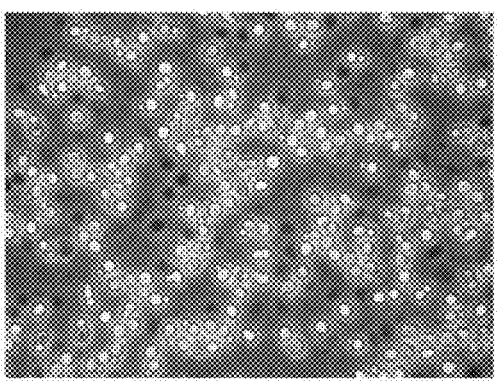
Figure 1E:
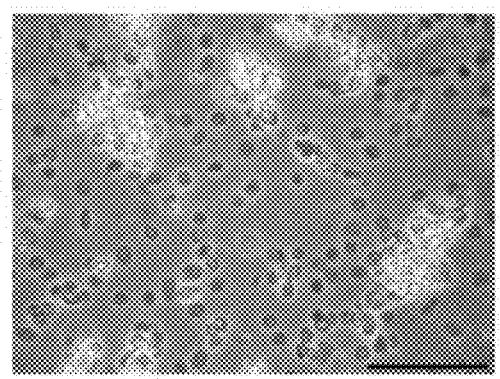

1. Erythrocytes Gave Rise to Abundant Vesicles at the Right $Ca^{2+}$-EDTA Concentrations Red blood cells (RBC) can vary in size due to pathologies but for the most part are consistently about 7.5-8 micrometers in diameter. When RBC were mixed with an equal volume of PBS (200 µl: 200 µl), RBC morphology appeared intact. When they were mixed with an equal volume of dd $H_2O$ (200 µl: 200 µl), RBC appeared to round up and their cell membranes became rough. When they were mixed with $Ca^{2+}$-EDTA and double deionized water at 200 µl: 50 µl: 50 µl: 100 µl (RBC: 1M $CaCl_2$: 390 mM EDTA: $H_2O$), RBC begin to form buds (indicated by arrows in FIG. 1C). The bud formation became the most abundant as the $Ca^{2+}$-EDTA concentrations were raised to a ratio of 200 µl: 70 µl: 70 µl: 60 µl (RBC: 1M $CaCl_2$: 390 mM EDTA: H2O; FIG. 1D). The buds were pinched off from RBC bodies to become vesicles. RBC lysed as the $Ca^{2+}$-EDTA concentrations were raised to above a ratio of 200 µl: 80 µl: 80 µl: 40 µl (RBC: 1M $CaCl_2$: 390 mM EDTA: $H_2O$; FIG. 1E). Those vesicles derived from erythrocytes having a diameter of sub-micrometer were defined as RDV, according to the present invention.

2. Nanometer-Sized, Iron-Containing RDV

Figure 2:
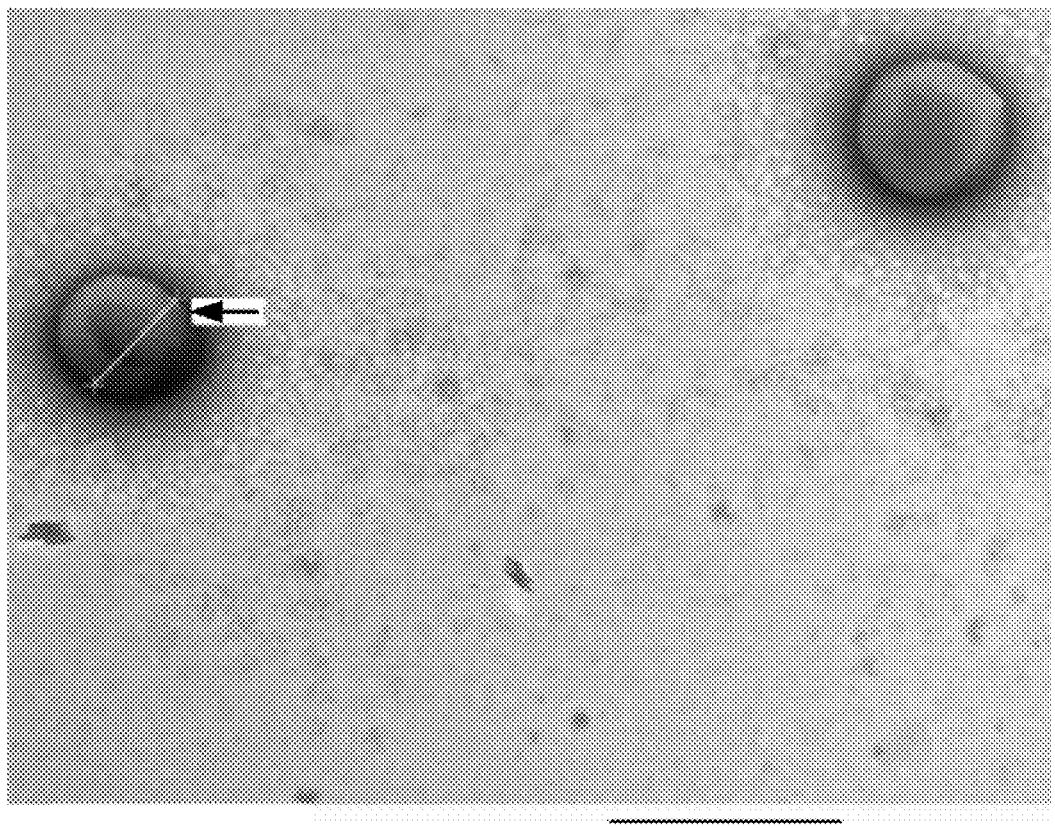
FIG. 2 is a transmission electron microscope image of the RDV. The arrow points to an RDV with a diameter of 259 nm. Scale bar: 500 nm.
Figures 13A, 13B:
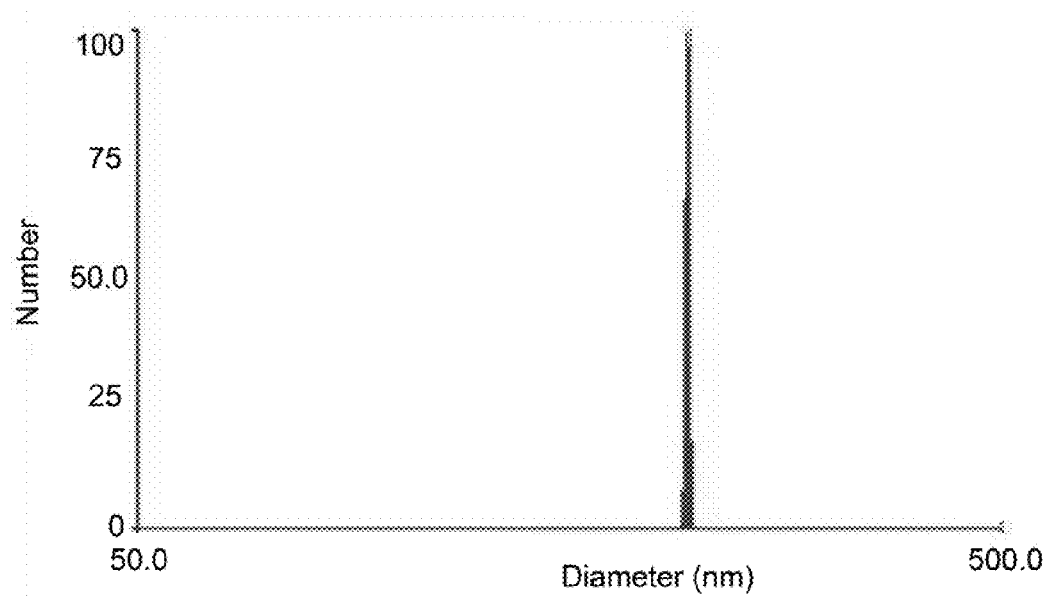
FIG. 13A is a histogram graph showing the distribution of RDV diameters.
FIG. 13B is a Table showing the measurements of RDV diameters in FIG. 13A.

FIG. 13 shows that the size of RDV distribution estimated by the particle size analyzer was ranging from about 213.4 to 218.5 nm, with a mean diameter at 215.9 nm. FIG. 2 shows a photograph of transmission electron micrograph (TEM) of RDV. Intrinsic iron in the total RDV tested was measured to be about 1.213 nmoles per 165 µg protein. The presence of iron increased the contrast of TEM image and thus facilitated observation of RDV under TEM. The diameter of RDV measured using TEM was about 259 nm, which was slightly larger than that estimated by the particle size analyzer. These nanometer-sized RDV are small enough to be engulfed by cells.

3. Nanometer-Sized RDV Carry Exogenous Substance Into Cells $Fe_3O_4$

Figure 3:
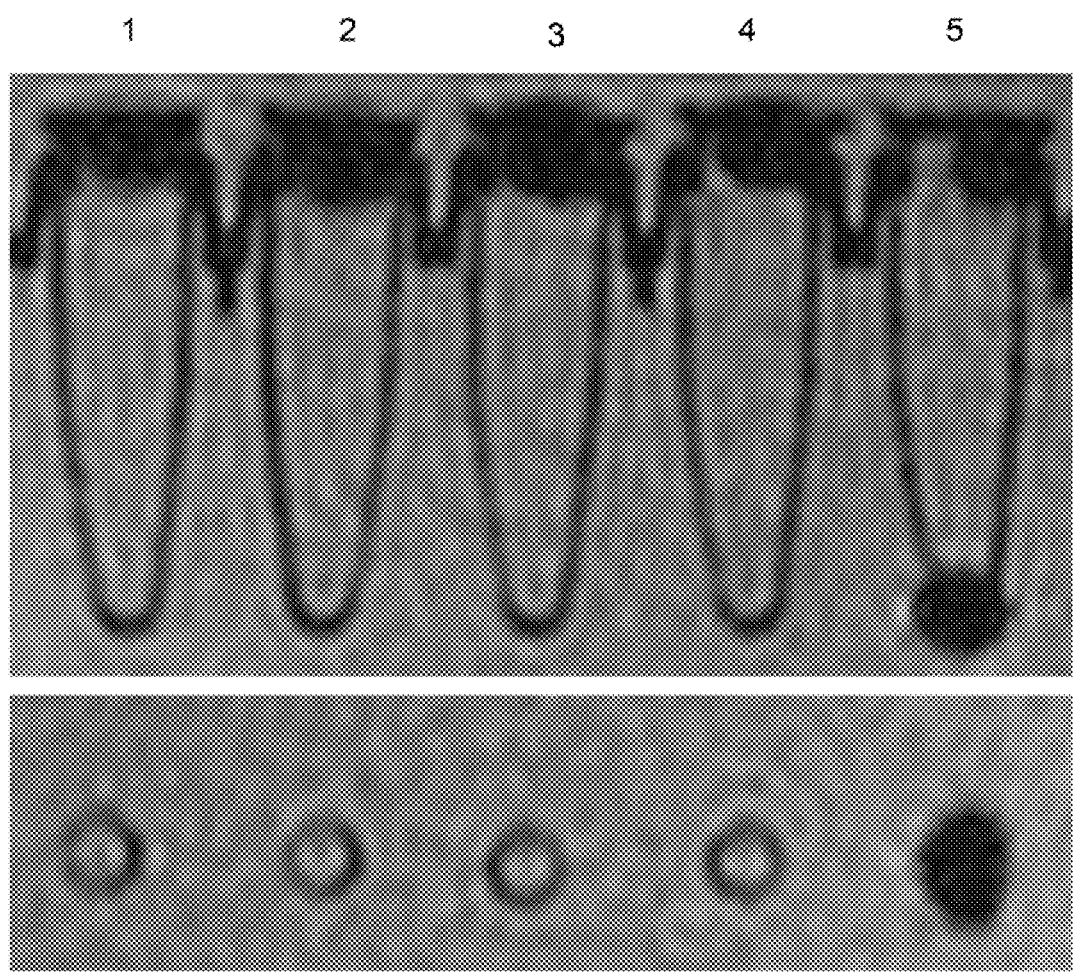
FIG. 3 are MRI images of human mesenchymal stem cell (hMSC) pellets showing RDV delivery of exogenous iron into the stem cells. Upper panel: vertical images of the tubes; lower panel: images of the pellets at the bottom of the tubes. 1: vehicle-treated; 2: RDV-treated; 3: $Fe_3O_4$-treated; 4: RDV-plus-$Fe_3O_4$-treated; 5: $Fe_3O_4$-encapsulated-RDV-treated.

To prove that RDV were capable of carrying an external substance into cells, $Fe_3O_4$, i.e., iron (II, III) oxide, (magnetite), was encapsulated into RDV, which were then delivered into hMSC. FIG. 3 shows the MRI images of hMSC pellets. Upper panel shows vertical images of the tubes. Bottom panel shows images of the pellets at the bottom of the tubes. Iron oxide-labeled cells were detected as darkened spots at the bottom of the test tubes. Tubes Nos. 1-4 contain the cell pellets of hMSCs treated with vehicle, RDV, $Fe_3O_4$, and RDV-plus-$Fe_3O_4$, respectively. Tube No. 5 contains a cell pellet of hMSCs treated with $Fe_3O_4$-encapsulated RDV. Only $Fe_3O_4$-encapsulated RDV-treated cells could be imaged as it showed a very dark spot image, which indicated that $Fe_3O_4$ had been successfully encapsulated into RDV and the $Fe_3O_4$-encapsulated RDV were able to be engulfed by hMSCs. The vehicle was composed of 100 µl of hypotonic solution and 2 ml of DMEM.

FITC

Flow Cytomery

Figure 5:
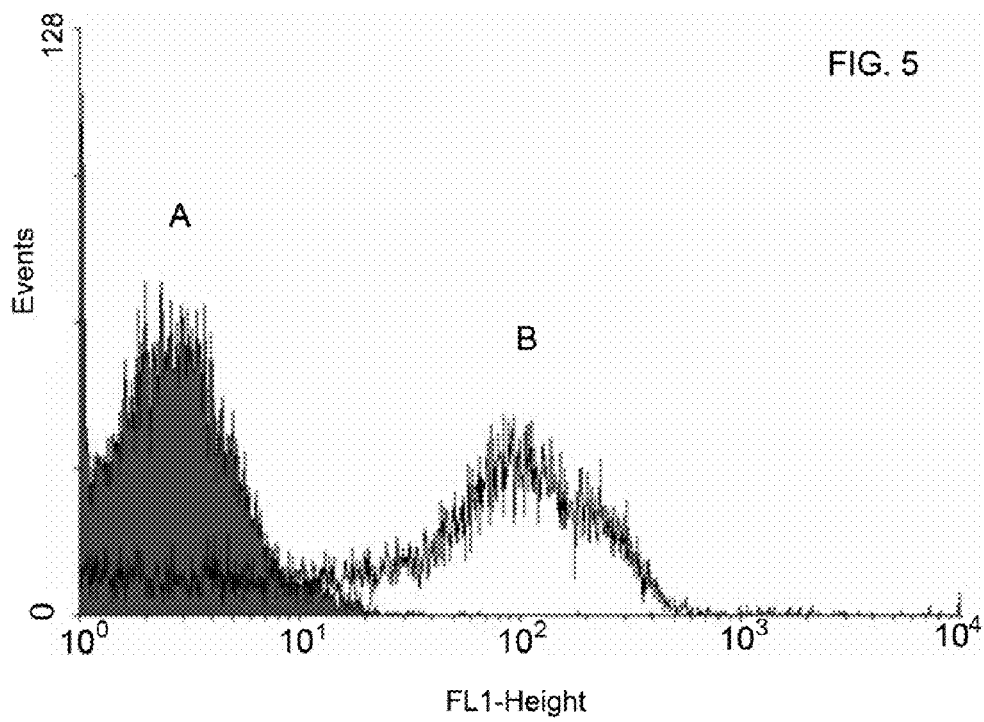
FIG. 5 is a graph of flow cytometry spectra showing fluorescence intensity of RDV with (B) or without (A) FITC encapsulation.

The RDV were encapsulated with various fluorescent molecules. In FIG. 5, peak A on the left-hand side of the diagram represents the RDV without FITC being encapsulated, and peak B on the right-hand side of the diagram represents the RDV that have successfully encapsulated FITC. The RDV that have encapsulated FITC exhibited a rightward shift in fluorescence intensity. The increase in fluorescence intensity confirms the encapsulation of the FITC within RDV.

Figure 6:
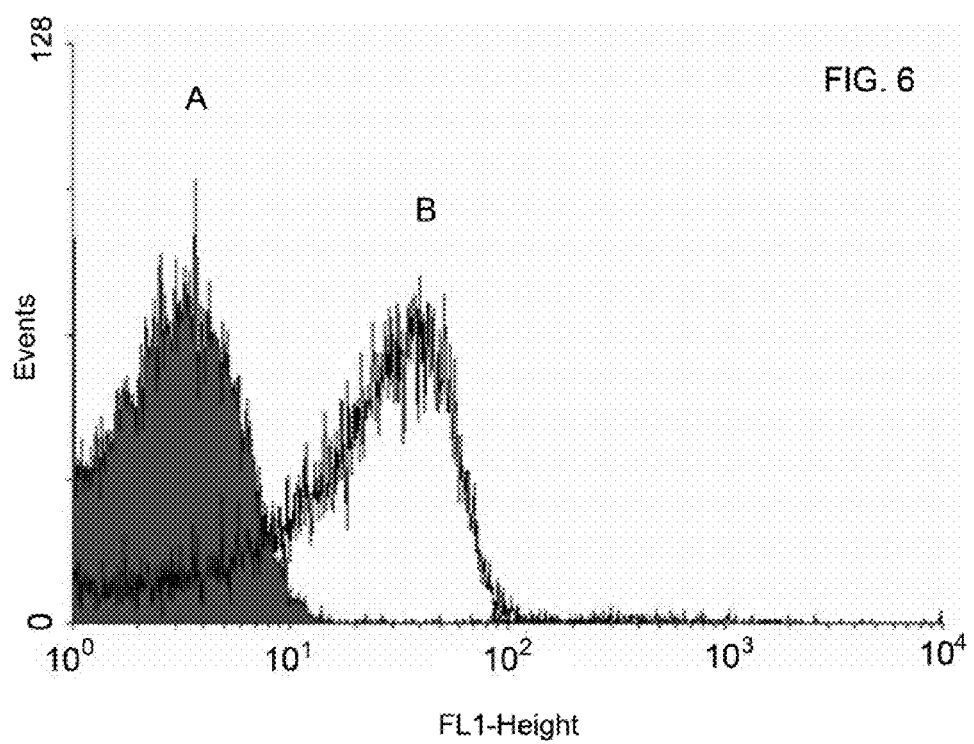
FIG. 6 is a graph of flow cytometry spectra showing NIH3T3 cells incubated with (B) or without (A) FITC-encapsulated RDV.

FIG. 6 shows a quantitative measure of RDV uptake by cells using flow cytometry. Peak A on the left-hand side of the diagram represents NIH3T3 cells incubated with RDV that did not encapsulate FITC. Peak B on the right-hand side of the diagram represents NIH3T3 cells treated with RDV that encapsulated FITC. The cells that engulfed FITC-encapsulated RDV exhibited a rightward sift in the peak of fluorescence intensity, which indicated that FITC was successfully delivered into NIH3T3 cells by RDV.

Confocal Microscopy

Figure 7:
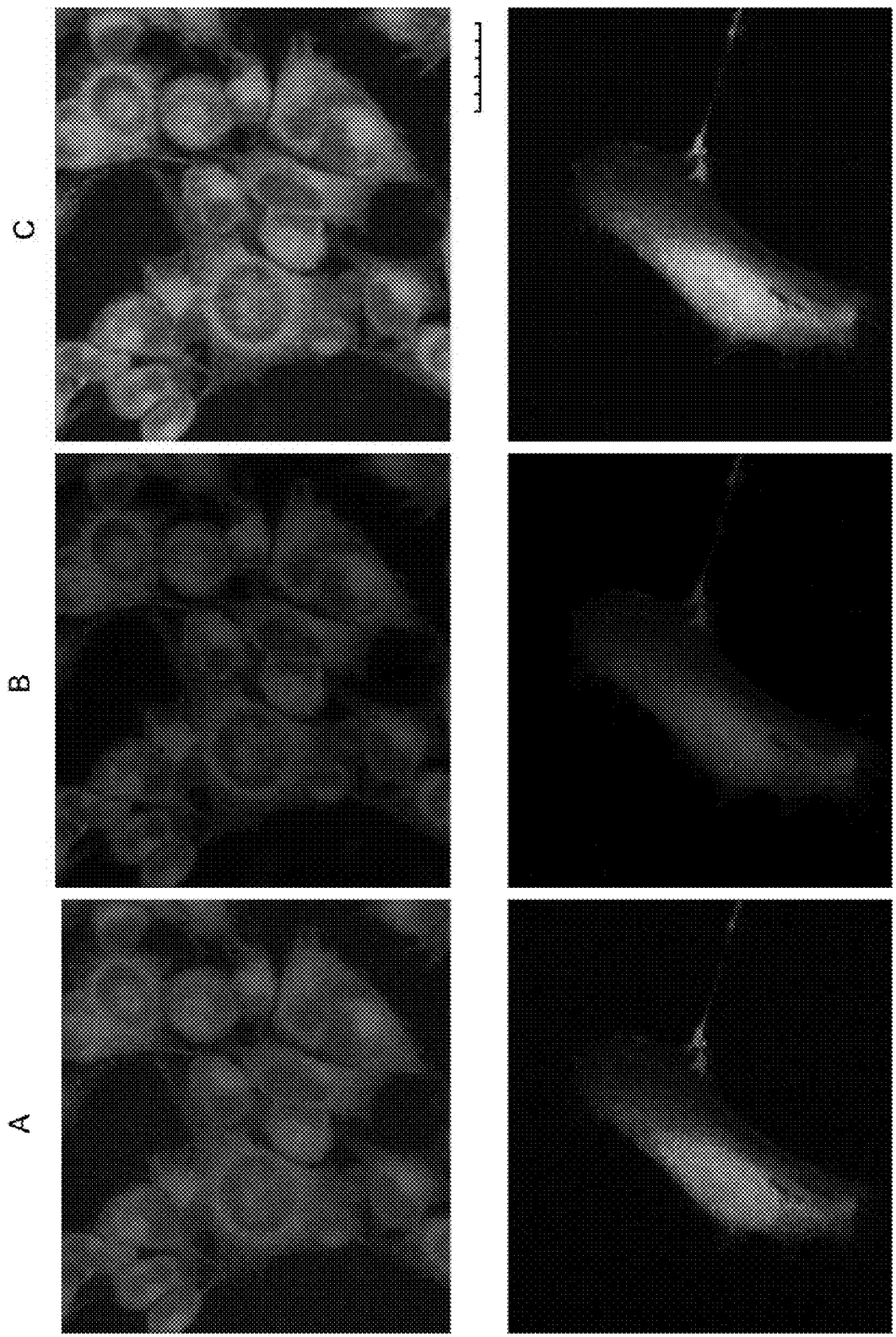
FIG. 7 are confocal microscope images showing cells treated with FITC-encapsulated RDV. Upper panel: B16 cells; Bottom panel: hMSCs. A: FITC fluorescence stained cells; B: Lysotracker fluorescence stained cells; C: overlay of images A and B. Scale bar: 25 μm.

To show that RDV function as a carrier for substances to be imaged and tracked in cells, FITC was encapsulated within RDV. Once the RDV were engulfed by B16 or hMSCs, the fluorescence was observed under confocal microscope as green fluorescence for FITC and FAM. The Lysotracker was observed as a red fluorescence localized to the lysosomes. In all cases, image overlays show that the engulfed RDV green fluorescence partially co-localized with the lysosomal red fluorescence. FIG. 7 shows B16 cells (upper panel) and hMSCs (bottom panel) after being treated with FITC-encapsulated RDV. A: FITC fluorescence stained cells; B: Lysotracker fluorescence stained cells; C: overlay of images A and B.

FITC-Taxol

Figure 8:
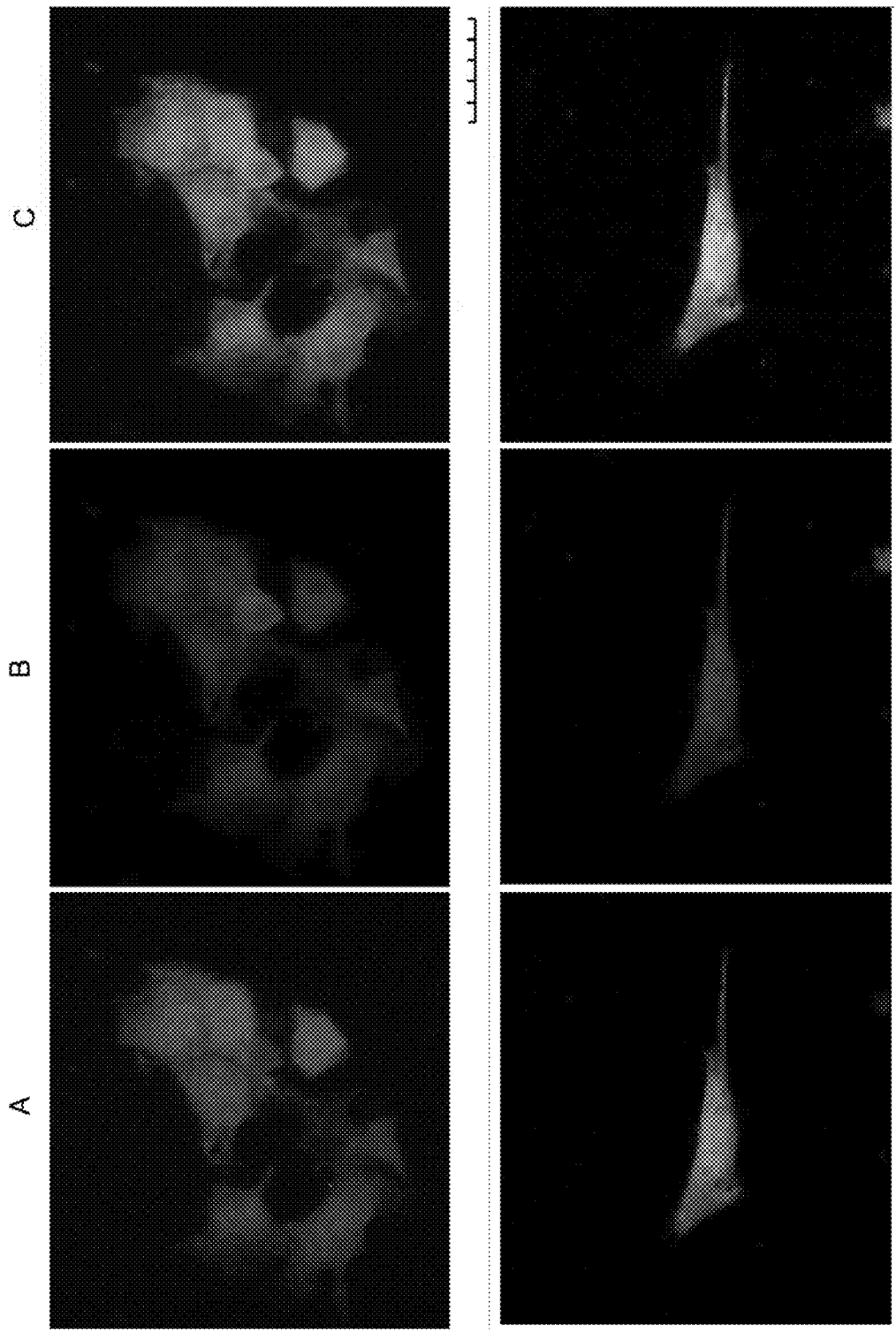
FIG. 8 are confocal microscope images showing cells treated with FITC-Taxol encapsulated RDV. Upper panel: B16 cells, Bottom panel: hMSCs. A: FITC fluorescence stained cells; B: Lysotracker fluorescence stained cells; C: overlay of images A and B. Scale bar: 25 μm.

FIG. 8 shows B16 cells (upper panel) and hMSCs (bottom panel) after treatment with FITC-Taxol encapsulated RDV. A: FITC fluorescence stained cells; B: Lysotracker fluorescence stained cells; C: the overlay of images A and B. The uptake of FITC-taxol into B16 (upper panel) and hMSCs (bottom panel) suggests that anti-cancer drugs can be encapsulated within RDV for a drug delivery system.

FAM-dsDNA, FAM-ssDNA, FAM-siRNA

Figure 9:
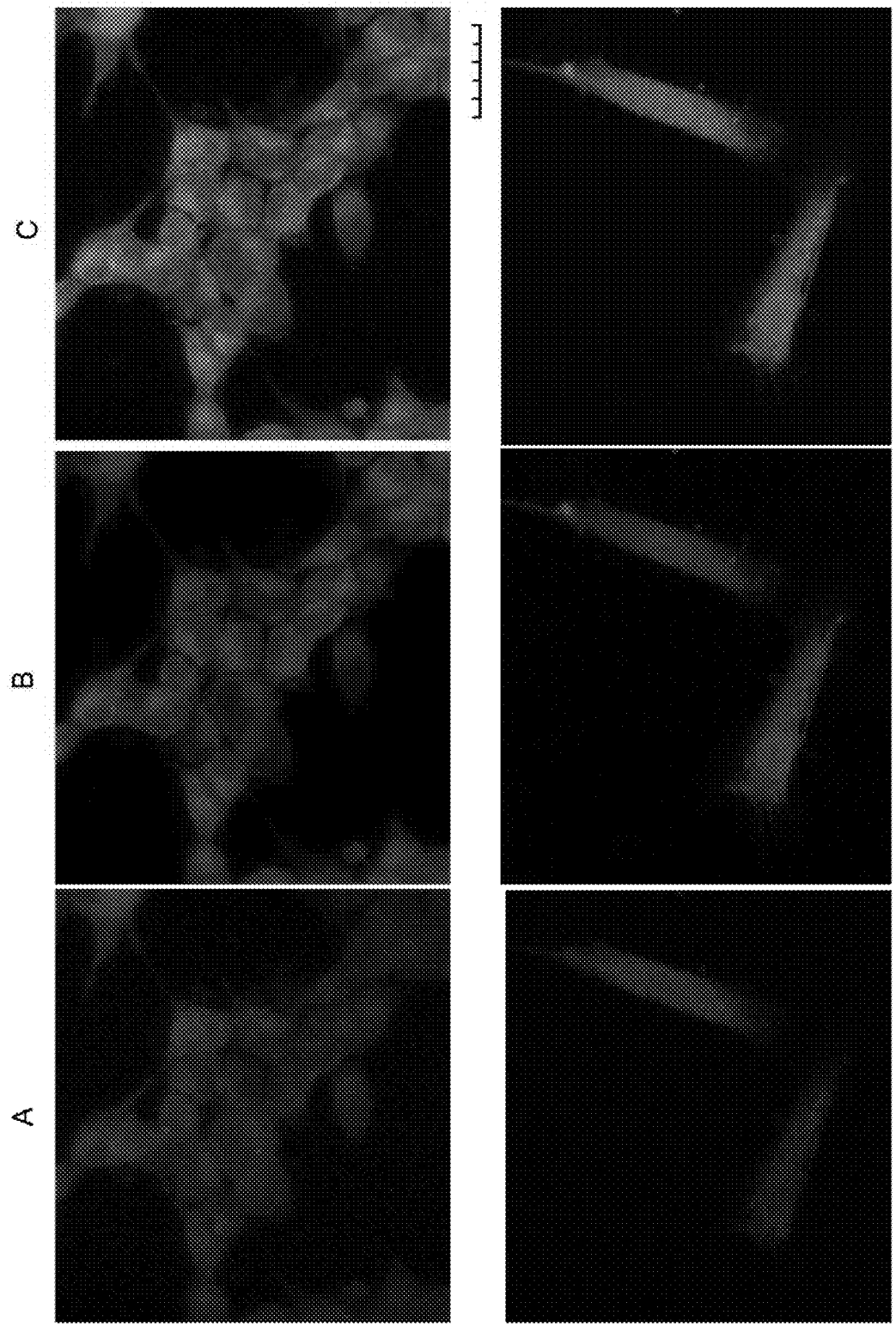
FIG. 9 are confocal microscope images showing B16 cells treated with FAM-dsDNA encapsulated RDV. Upper panel: B16 cells. Bottom panel: hMSCs. A: FITC fluorescence stained cells; B: Lysotracker fluorescence stained cells; C: overlay of images A and B. Scale bar: 25 μm.

The potential application of PDV to a delivery system for gene therapy was shown by the uptake of FAM-dsDNA, FAM-ssDNA and FAM-siRNA into B16 and hMSCs. FIG. 9 shows B16 cells (upper panel) and hMSCs (bottom panel) after treatment with FAM-dsDNA encapsulated RDV. A: FITC fluorescence stained cells; B: Lysotracker fluorescence stained cells; C: overlay of images A and B. The siRNA was a double-stranded RNA composing of both sense and antisense strand. Being used as a negative control, the siRNA didn't target any protein.

Figure 10:
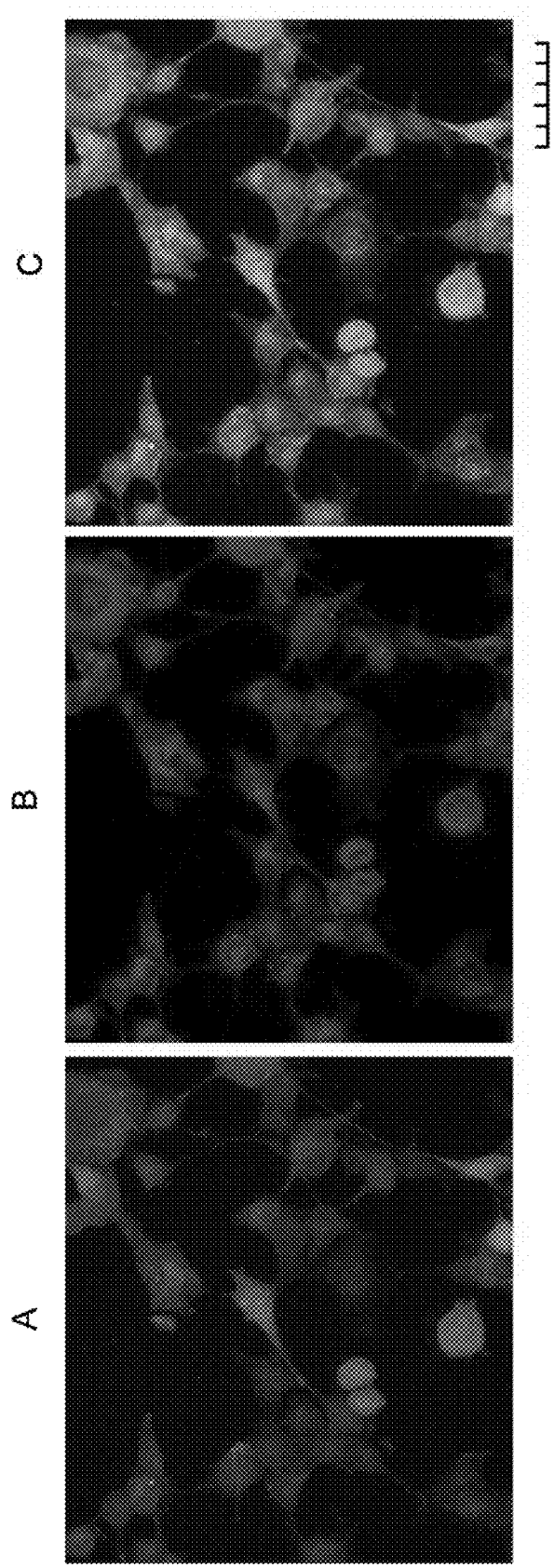
FIG. 10 are confocal microscope images showing B16 cells treated with FAM-ssDNA-encapsulated RDV. A: FITC fluorescence stained cells; B: Lysotracker fluorescence stained cells; C: overlay of images A and B. Scale bar: 50 μm.
Figure 11:
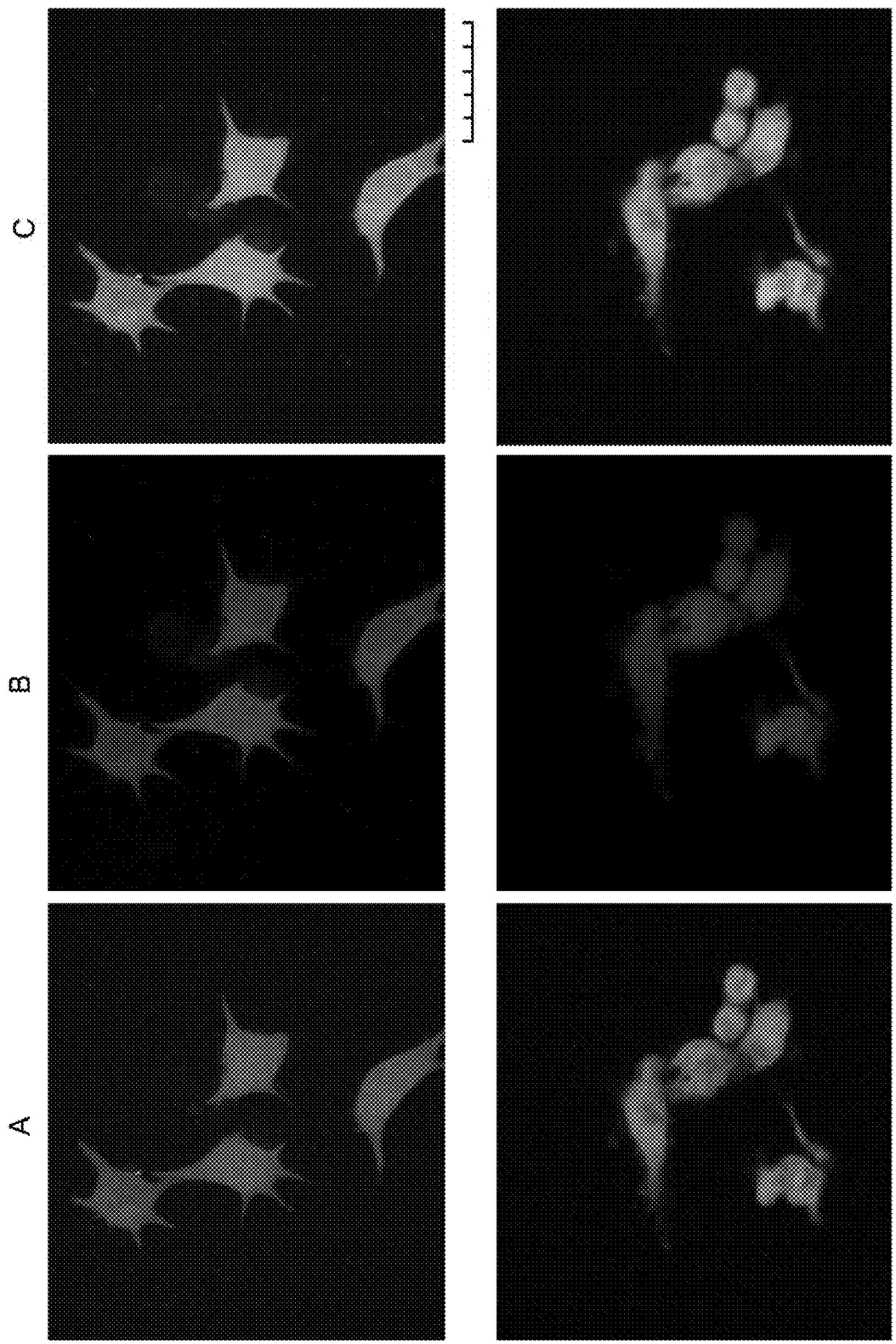
FIG. 11 are confocal microscope images showing cells treated with FAM-siRNA encapsulated RDV. Upper panel: B16 cells. Bottom panel: hMSCs. A: FITC fluorescence stained cells; B: Lysotracker fluorescence stained cells; C: overlay of images A and B. Scale bar: 50 μm.

FIG. 10 shows B16 cells after being treated with FAM-ssDNA-encapsulated RDV. A: FITC fluorescence stained cells; B: Lysotracker fluorescence stained cells; C: the overlay of images A and B. FIG. 11 shows B16 cells (upper panel) and hMSCs (bottom panel) after being treated with FAM-siRNA encapsulated RDV. A: FITC fluorescence stained cells; B: Lysotracker fluorescence stained cells; C: the overlay of images A and B.

4. RDV as a Cell-Labeling Agent for Tracking Cells

Figure 4:
FIG. 4 is an MR image in mice showing the magnetically labeled hMSCs on the left side of the brain, as indicated by the circle.

To test the utility of RDV as a cell-tracking agent in vivo, hMSCs having been treated with iron oxide-encapsulated RDV were injected into the left side of the mouse brain, and the cells treated with vehicles as a control were injected into the right side of the mouse brain. The mouse was then imaged using MRI. As shown in FIG. 4, only the left side but not the right side of the brain showed a dark spot image (as circled).

5. RDV as Harmless Potential Nanoparticle Tracing and Delivery System

Figure 12:
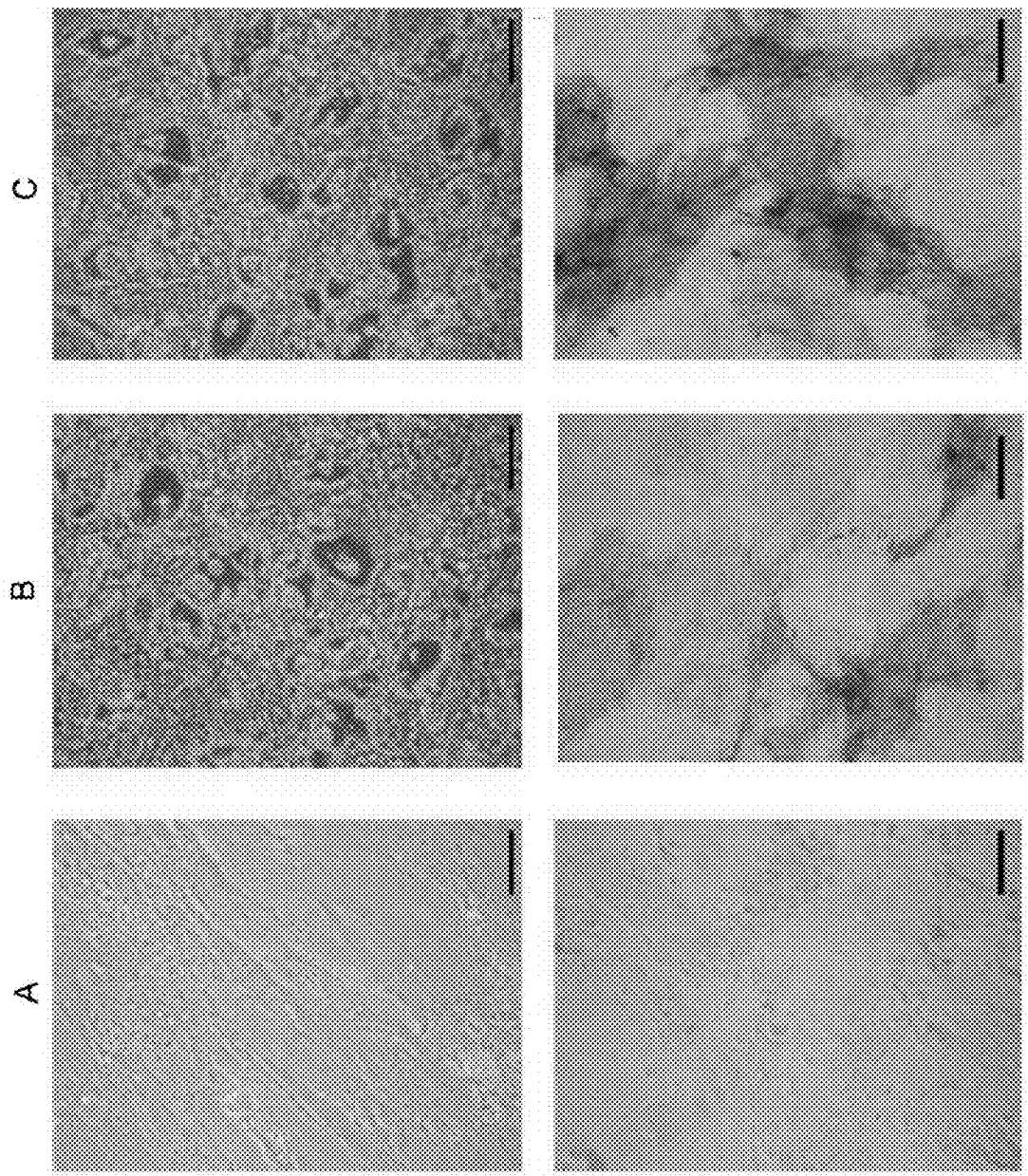
FIG. 12 are images showing histochemically stained cells. Upper panels: oil-red staining; A: vehicle-treated hMSCs grown in normal culture medium; B: vehicle treated, grown in adipogenic medium; C: RDV-treated, grown in adipogenic medium. Bottom panels: fast-blue staining; A: vehicle-treated hMSCs grown in normal culture medium; B: vehicle treated, grown in osteogenic medium; C: RDV-treated, grown in osteogenic medium. Scale bars: 50 μm.

To test the biosafety of RDV, hMSCs after being treated with RDV alone were examined to investigate whether their differentiation potential was compromised. FIG. 12 shows histochemically stained cells using a phase contrast microscope (Olympus). Adipocytes were stained with Oil Red for detecting intracellular fat in red. Osteocytes were stained with Fast Blue (Sigma) for detecting intracellular alkaline phosphatase in violet. The results of Oil Red and Fast Blue staining were shown in the upper and bottom panels, respectively. The vehicle-treated hMSCs grown in a normal culture medium did not show any Oil Red staining (upper panel, A), which indicated that no cells were differentiated into adipocytes in the normal medium. The vehicle-treated hMSCs grown in adipogenic medium were capable of differentiation into adipocytes (upper panel, B). Likewise, the RDV-treated hMSCs grown in adipogenic medium were capable of differentiation into adipocytes as well (upper panel, C). For Fast Blue staining, the vehicle-treated hMSCs grown in normal culture medium did not show any Fast Blue staining (bottom panel, A), which indicated that no cells were differentiated into osteocytes. The vehicle-treated hMSCs grown in osteogenic medium showed Fast Blue staining, which indicated that stem cells were induced to differentiate into osteocytes in the osteogenic medium (bottom panel, B). Likewise, RDV-treated hMSCs grown in osteogenic medium showed Fast Blue staining, which indicated that stem cells were induced to differentiate into osteocytes in the osteogenic medium. The results indicated that RDV internalization did not affect the differentiation potential of hMSCs into adipocytes (upper panel) and osteocytes (bottom panel). RDV did not affect cell viability as well (data not shown).

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of delivering an exogenous substance into a cell, comprising:
   (a) providing a red blood cell (RBC);
   (b) treating the RBC with a $Ca^{2+}$-EGTA solution to obtain an isolated red blood cell membrane-derived vesicle (RDV), wherein the RDV is cytoskeleton free and has at least one erythrocyte protein present in the vesicle;
   (c) encapsulating the exogenous substance into the RDV to obtain an exogenous substance-loaded RDV;
   (d) contacting the cell with the exogenous substance-loaded RDV; and
   (e) allowing the cell to engulf the exogenous substance-loaded RDV to obtain a cell with the exogenous substance encapsulated within the RDV, thereby delivering the exogenous substance into the cell.

2. A method of delivering an exogenous substance into a cell, comprising:
   (a) contacting the cell with an exogenous substance-loaded RDV, the exogenous substance-loaded RDV comprising:
      (i) an isolated red blood cell membrane-derived vesicle (RDV), the RDV being free of cytoskeleton and having at least one erythrocyte protein present in the vesicle; and
      (ii) the exogenous substance, encapsulated within the RDV; and
   (b) allowing the cell to engulf the exogenous substance-loaded RDV to obtain a cell with the exogenous substance encapsulated within the RDV, thereby delivering the exogenous substance into the cell.

3. The method of claim 2, wherein the RDV has no modification on the membrane surface thereof.

4. The method of claim 2, wherein the RDV contains intrinsic iron.

5. The method of claim 2, wherein the at least one erythrocyte protein is hemoglobin.

6. The method of claim 2, wherein the at least one erythrocyte protein is a membrane bound glycoprotein.

7. The method of claim 6, wherein the membrane bound glycoprotein is selected from the group consisting of band 3 protein, PAS-1, PAS-2 and PAS-3 proteins.

8. The method of claim 2, wherein the exogenous substance that is delivered into the cell remains encapsulated within the RDV.

9. The method of claim 2, wherein the exogenous substance encapsulated within the RDV is localized within a lysosome of the cell.

10. The method of claim 2, wherein the exogenous substance is at least one selected from the group consisting of a superparamagnetic compound, a fluorescent compound, and any combination thereof.

11. The method of claim 2, wherein the cell is a stem cell and the exogenous substance is a superparamagnetic compound.

12. The method of claim 11, wherein the superparamagnetic compound is $Fe_3O_4$.

13. The method of claim 2, wherein the cell is a mesenchymal stem cell.

14. A method of tracking a, stem cell in a mammalian subject, comprising:

(a) contacting the stem cell with a superparamagnetic compound-loaded RDV, the superparamagnetic compound-loaded RDV-comprising:

(i) an isolated red blood cell membrane-derived vesicle (RDV), the RDV being free of cytoskeleton and having at least one erythrocyte protein present in the vesicle; and (ii) a superparamagnetic compound, encapsulated within the RDV; and (b) allowing the stem cell to engulf the superparamagnetic compound-loaded RDV to obtain the stem cell with the superparamagnetic compound encapsulated within the RDV;

(c) administering to a mammalian subject in need thereof the stem cell with the superparamagnetic compound encapsulated within the RDV; and (d) tracking the superparamagnetic compound within the stem cell by magnetic resonance imaging (MRI) in the mammalian subject;

wherein the stem cell and RDV are autologous to the mammalian subject in need thereof.

15. The method of claim 14, wherein the RDV has no modification on the membrane surface thereof.

16. The method of claim 1, wherein the RDV contains intrinsic iron.

17. The method of claim 1, wherein the at least one erythrocyte protein is hemoglobin.

18. The method of claim 1, wherein the RDV has a diameter of no more than 400, 350, or 300 nanometers.

* * * * *